United States Patent
Stamler et al.

(10) Patent No.: US 9,063,160 B2
(45) Date of Patent: Jun. 23, 2015

(54) METHOD FOR LIBERATING AND DETECTING NITRIC OXIDE FROM NITROSOTHIOLS AND IRON NITROSYLS IN BLOOD

(75) Inventors: Jonathan S. Stamler, Chapel Hill, NC (US); Michael Angelo, Durham, NC (US)

(73) Assignee: Duke University, Durham, NC (US)

( * ) Notice: Subject to any disclaimer, the term of this patent is extended or adjusted under 35 U.S.C. 154(b) by 1192 days.

(21) Appl. No.: 12/668,211

(22) PCT Filed: Jul. 15, 2008

(86) PCT No.: PCT/US2008/008630
§ 371 (c)(1),
(2), (4) Date: Sep. 29, 2010

(87) PCT Pub. No.: WO2009/014616
PCT Pub. Date: Jan. 29, 2009

(65) Prior Publication Data
US 2011/0008815 A1 Jan. 13, 2011

Related U.S. Application Data

(60) Provisional application No. 60/935,121, filed on Jul. 26, 2007.

(51) Int. Cl.
| | |
|---|---|
| *G01N 33/49* | (2006.01) |
| *G01N 33/50* | (2006.01) |
| *G01N 33/497* | (2006.01) |
| *G01N 23/00* | (2006.01) |
| *G01N 33/84* | (2006.01) |
| *A61B 5/00* | (2006.01) |
| *A61B 5/145* | (2006.01) |
| *G01N 27/416* | (2006.01) |
| *A61B 5/15* | (2006.01) |

(52) U.S. Cl.
CPC .............. *G01N 33/84* (2013.01); *A61B 5/0059* (2013.01); *A61B 5/1405* (2013.01); *A61B 5/14546* (2013.01); *A61B 5/412* (2013.01); *G01N 27/416* (2013.01)
USPC ............................ 436/68; 436/116; 435/287.1

(58) Field of Classification Search
CPC ..... G01N 33/49; G01N 33/50; G01N 33/497; G01N 23/00; C12M 1/34
See application file for complete search history.

(56) References Cited

U.S. PATENT DOCUMENTS

| | | | |
|---|---|---|---|
| 5,174,291 A | 12/1992 | Schoonen et al. | |
| 5,366,903 A | 11/1994 | Lundsgaard et al. | |
| 5,374,710 A * | 12/1994 | Tsien et al. ................... | 534/552 |
| 5,459,076 A | 10/1995 | Stamler et al. | |
| 5,891,735 A * | 4/1999 | Stamler ........................ | 436/66 |
| 6,791,689 B1 * | 9/2004 | Weckstrom .................. | 356/437 |
| 7,090,648 B2 * | 8/2006 | Sackner et al. .................. | 601/1 |
| 7,122,027 B2 * | 10/2006 | Trescony et al. ........... | 604/891.1 |
| 2005/0054908 A1 | 3/2005 | Blank et al. | |
| 2006/0074282 A1 | 4/2006 | Ward et al. | |
| 2007/0149868 A1 | 6/2007 | Blank et al. | |

FOREIGN PATENT DOCUMENTS

| | | |
|---|---|---|
| AU | 2008279755 B2 | 4/2014 |
| JP | 6-510605 A | 11/1994 |
| JP | 8-220054 A | 8/1996 |
| JP | 2001-281213 A | 10/2001 |
| JP | 2005-127928 A | 5/2005 |
| JP | 2005-257647 A | 9/2005 |

OTHER PUBLICATIONS

Sondur, Rajshekar, Metallo Protein Induced Nitric Oxide Release from Nitrosothiols, Dec. 2004, Sondur, pp. 1-118, especially p. 20.
Alpert et al., Detection of S-Nitrosothiols and Other Nitric Oxide Derivatives by Photolysis-Chemiluminescence Spectrometry, Anal. Biochem. 245, 1997, pp. 1-7.
Vladimirov et al., "NO-hemoglobin may be a light-sensitive source of nitric oxide both in solution and in red blood cells", Journal of Photochemistry and Photobiology, vol. 59, 2000, pp. 115-122.
"Australian Application Serial No. 2008279755, Office Action mailed Nov. 26, 2012", 3 pgs.
"Australian Application Serial No. 2008279755, Response filed Nov. 25, 2013 to Office Action mailed Nov. 26, 2012", 10 pgs.
"European Application Serial No. 08794495.5, Examination Notification Art. 94(3) mailed Dec. 10, 2013", 4 pgs.
"European Application Serial No. 08794495.5, Extended European Search Report mailed Feb. 22, 2013", 7 pgs.
"European Application Serial No. 08794495.5, Office Action mailed Mar. 8, 2010", 2 pgs.
"European Application Serial No. 08794495.5, Office Action mailed Mar. 12, 2013", 1 pg.

(Continued)

*Primary Examiner* — Blaine Lankford
*Assistant Examiner* — Charles Zoltan Constantine
(74) *Attorney, Agent, or Firm* — Schwegman Lundberg & Woessner, P.A.

(57) ABSTRACT

Amount of combined nitric oxide or nitric oxide present as iron nitrosyls in a blood sample is determined by directing a low power electromagnetic radiation beam at a blood sample to liberate nitric oxide gas, dissolving the liberated nitric oxide gas and electrochemically detecting amount of dissolved nitric oxide gas.

12 Claims, 3 Drawing Sheets

(56) References Cited

OTHER PUBLICATIONS

"European Application Serial No. 08794495.5, Response filed Apr. 10, 2014 to Examination Notification Art. 94(3) mailed Dec. 10, 2013", 20 pgs.

"European Application Serial No. 08794495.5, Response filed Sep. 10, 2013 to Office Action mailed Mar. 12, 2013", 8 pgs.

"Japanese Application Serial No. 2010-518179, Amendment filed May 19, 2010", (w/ Machine Translation), 6 pgs.

"Japanese Application Serial No. 2010-518179, Office Action mailed Jun. 18, 2013", (W/ English Summary), 5 pgs.

"Japanese Application Serial No. 2010-518179, Response filed Dec. 11, 2012 to Office Action mailed Jun. 12, 2012", (w/ Machine Translation), 13 pgs.

\* cited by examiner

METHOD FOR LIBERATING AND DETECTING NITRIC OXIDE FROM NITROSOTHIOLS AND IRON NITROSYLS IN BLOOD

CROSS-REFERENCE TO RELATED APPLICATIONS

This application claims the benefit of U.S. Provisional Patent Application No. 60/935,121, filed Jul. 26, 2007, the whole of which is incorporated herein by reference.

TECHNICAL FIELD

This invention is directed to determining amount of combined nitric oxide in blood. There is a need for this determination in a clinical setting. For example, blood nitric oxide is depressed in patients with sickle cell disease and patients with pulmonary hypertension and determination of this is useful to confirm diagnosis. See Pawloski, J. R., et al., PNAS 102(7), 2531-2536 (2005) and McMahon, T. J., et al. PNAS 102(41), 14801-14806 (Nov. 11, 2005). Moreover, blood nitric oxide is elevated in those with sepsis; see Liu, L., et al., Cell 116, 617-628 (2004); and determination of this is useful to confirm diagnosis.

BACKGROUND OF THE INVENTION

It is known that iron bound nitric oxide and S-nitrosothiols in blood samples degrade and liberate free nitric oxide when the samples are irradiated with ultraviolet (UV) electromagnetic radiation, allowing detection of amount of free nitric oxide.

In existing machines for detecting amount of nitric oxide bound to hemoglobin and in nitrosothiols in blood, a 150 W mercury vapor lamp is used as a high intensity, broad spectrum UV source that irradiates liquid blood-containing samples as they flow through a Pyrex® glass coil. The use of a 150 W mercury vapor lamp requires a large surface area sample. A flow-through process is necessary to provide the large surface area. A flow-through stream is aerated with a helium carrier gas stream, allowing free nitric oxide gas to be transported to a separate unit that houses a nitric oxide detector where the freed nitric oxide is reacted with ozone to generate light (chemiluminescence) which is detected by a photomultiplier tube. This method is described in Stamler et al. U.S. Pat. No. 5,459,076 and in Stamler U.S. Pat. No. 5,891,735. This method while useful in a research setting is too cumbersome for a clinical setting. The narrow diameter of the tubing through which the samples pass and elevated temperatures encountered, prohibit measurement on turbid samples in the glass coil of the tubing. Furthermore, the glass coil needs to be reused, requiring cleaning between runs.

Lucht et al. U.S. Pat. No. 6,982,426 teaches a nitric oxide sensor and method comprising passing a signal beam from a laser in a crystal through a sample into a photomultiplier tube and detection of output ultraviolet radiation which indicates level of nitric oxide by comparison with control based on nitric oxide absorption of ultraviolet radiation. Measurements are made by photomultiplier tubes. The apparatus and method are not useful for biological samples and lack sensitivity.

Sackner et al. U.S. Pat. No. 7,090,648 teaches light/laser therapy in wound healing and indicates this therapy releases nitric oxide from hemoglobin and states that this has the potential to enhance wound healing.

SUMMARY OF THE INVENTION

It has been discovered herein that use of a low power laser electromagnetic radiation beam or of a low power light-emitting diode electromagnetic radiation to liberate nitric oxide gas from a blood sample, allows use on a stationary small volume, small surface area sample which may constitute whole cells and use of a disposable sample container. As used herein the term "low power" means less than 100 milliwatts, e.g. 30 to 60 milliwatts, e.g. 50 milliwatts.

A first embodiment herein is directed at a method for liberating nitric oxide gas from combined nitric oxide in a blood sample, comprising directing low power electromagnetic radiation from a laser or a light-emitting diode at the blood sample for a period sufficient to release free nitric oxide from combined nitric oxide which is present in the blood sample.

As used herein the term "combined nitric oxide" means nitric oxide present as nitrosothiols and as iron nitrosyls. As used herein the term iron nitrosyls means FeNO and any other N-oxides bound to iron that liberate nitric oxide.

A second embodiment herein is directed at a method for determining amount of nitric oxide present as combined nitric oxide in a blood sample, comprising the steps of:

(a) introducing a sample of the blood to be analyzed for amount of combined nitric oxide therein, into a sample containing zone having a front side which is electromagnetic radiation transparent and a rear side which is porous to the extent of permitting nitric oxide gas to pass therethrough while preventing protein from passing therethrough;

(b) directing low power electromagnetic radiation at said front side to cause liberation of nitric oxide gas from combined nitric oxide and passage of the liberated nitric oxide gas from said rear side;

(c) providing a solvent containing zone to dissolve the liberated nitric oxide gas that has passed through said rear side where the solvent of the solvent-containing zone is one that dissolves nitric oxide gas;

(d) electrochemically detecting amount of dissolved nitric oxide gas in the solvent which corresponds to the total amount of nitric oxide present as combined nitric oxide in the sample.

A third embodiment herein is directed at a method for determining amount of nitric oxide present as combined nitric oxide in blood and also amount of nitric oxide present as iron nitrosyls in blood comprising the steps of (a) obtaining two samples of blood from the same source (e.g., patient), each comprising combined nitric oxide present as nitrosothiols and iron nitrosyls, where one of the samples is denoted as the first sample and the other of the samples is denoted as the second sample;

(b) treating the second sample with a nitrosothiols degrading agent, e.g. a mercury compound, to cause decomposition of nitrosothiols therein to nitrous acid;

(c) analyzing for amount of nitric oxide present as combined nitric oxide in the first sample by the steps of (i) introducing the first sample into a first sample containing zone which has a front side which is electromagnetic radiation transparent and a rear side which is porous to the extent of permitting nitric oxide gas to pass therethrough while preventing protein from passing therethrough, (ii) directing a low power electromagnetic radiation at said front side of the first sample containing zone to cause liberation of nitric oxide gas from combined nitric oxide and passage of the liberated nitric oxide gas through said rear side, (iii) providing a first solvent containing zone to dissolve the liberated nitric oxide gas that has passed through said rear side where the solvent is one that dissolves nitric oxide gas, (iv) electrochemically detecting amount of dissolved nitric oxide in the first solvent containing zone which corresponds to the total amount of nitric oxide present as combined nitric oxide in said first sample, (d) analyzing for amount of nitric oxide present as iron nitrosyls in the step (b) treated second sample by the steps of
(i) introducing the step (b) treated second sample into a second sample containing zone which has a front side which is electromagnetic radiation transparent and a rear side which is porous to the extent of permitting nitric oxide gas to pass therethrough while preventing protein from passing therethrough, (ii) directing a low power electromagnetic radiation at said front side of the second sample containing zone to cause liberation of nitric oxide gas from said iron nitrosyls and passing of the liberated nitric oxide gas through said rear side, (iii) providing a second solvent containing zone to dissolve the liberated nitric oxide gas that has passed through said rear side where the solvent is one that dissolves nitric oxide, (iv) electrochemically detecting amount of dissolved nitric oxide in the second solvent containing zone which corresponds to the amount of nitric oxide present as iron nitrosyls in said second sample.

In a variation of the third embodiment, step (e) is omitted and only amount of nitric oxide present as iron nitrosyls is analyzed for.

DETAILED DESCRIPTION

Figure 1:
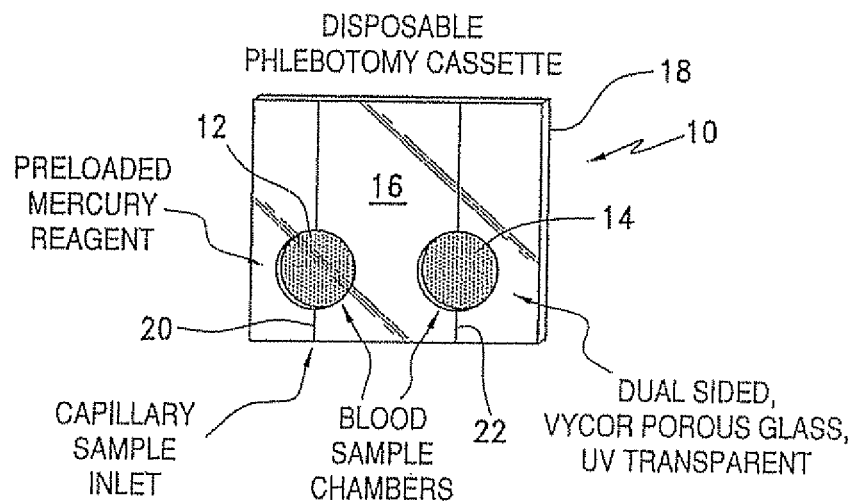
FIG. 1 depicts a disposable phlebotomy cassette for holding the first sample and treated second sample of the third embodiment.

A low power radiation emitter is used in all embodiments herein because it has been found that such a radiation emitter can be used to deliver a large dose of radiation to a stationary small sample of blood to liberate nitric oxide gas therefrom. The dose of energy delivered by the emitter is proportional to the power of the emitter and inversely proportional to the diameter of the emitter beam.

We turn now to the first embodiment.

The low power electromagnetic radiation can preferably be ultraviolet radiation having a wavelength ranging from 300 to 400 nm, very preferably from 325 to 355 nm. This can be provided by a low power ultraviolet laser especially a neodymium-doped yttrium aluminum garnet laser, i.e. a $Nd:Y_3Al_5O_{12}$ laser, which emits ultraviolet radiation or by a tunable laser tuned, e.g. to provide 325 to 355 nm radiation, commercially available from Opotek, Inc. (California) in the specified range. This low power ultraviolet radiation can also be provided by an ultraviolet light-emitting diode which is commercially available to emit ultraviolet radiation in these wavelengths.

The low power electromagnetic radiation can also be ultraviolet radiation having a wavelength ranging from 210 to 220 nm, e.g. 220 nm. Light-emitting diodes emitting ultraviolet radiation down to 210 nm wavelength are available, e.g. aluminum gallium indium nitride light emitting diodes emitting down to 210 nm wavelength are available.

The low power electromagnetic radiation can also be low power visible electromagnetic radiation having a wavelength ranging from 500 to 600 nm. This can be provided by a low power green LED lamp which is commercially available.

The low power electromagnetic radiation can also be low power near infrared radiation (700-1400 nm wavelength). This can be provided by a near-infrared light-emitting diode which is commercially available.

The 210-220 nm, 300-400, 500-600 nm and near-infrared wavelength emissions referred to above degrade nitrosothiols to gaseous nitric oxide and to provide adequate absorbance into iron nitrosyls (characteristic moiety for nitric oxide bound to heme) to liberate gaseous nitric oxide therefrom.

We turn now the blood sample. It has a small surface area and small volume. For example, it can have a diameter ranging, for example, from 2 to 6 mm with a transverse dimension of, for example, 0.5 to 1 mm.

The blood sample is readily obtained by pricking a finger with a sharp and may be loaded into a sample holder by capillary action.

If it is only desired to liberate nitric oxide from iron nitrosyls in blood, the blood sample is treated with metal ion (e.g., mercury (II) ion or $Ag^+$ ion), e.g. mercury chloride, or organic mercury (e.g., methyl mercury) to degrade nitrosothiols in the sample to nitrous acid (which does not liberate nitric oxide on receiving electromagnetic radiation energy). This can be carried out by providing nitrosothiol degrading agent in a sample containing (holding) zone before loading of blood sample therein. In this case the radiation emitter is directed at the blood sample which has been treated to degrade nitrosothiol and the term "blood sample" used in the description of the first embodiment includes untreated blood sample as well as nitrosothiols degraded treated (treated with nitrosothiols degrading agent) blood sample.

A laser or light-emitting diode is positioned, e.g., up to a foot, for example, 6 to 10 inches from the sample. This distance can be reduced if fiber optic transmission of emitter beam is utilized.

An electromagnetic radiation beam is directed at the sample and preferably on reaching the sample, has a cross-sectional area the same as and coextensive with the cross-sectional area of the sample.

The electromagnetic radiation treatment causes photolysis of nitrosothiols and iron nitrosyls in a blood sample or a treated blood sample to release gaseous nitric oxide and is continued until nitric oxide gas emission is no longer noted.

We turn now to the second embodiment.

The sample containing zone has dimensions and volume described in conjunction with the first embodiment.

The front side (wall) of the sample containing zone is electromagnetic radiation transparent so the front wall of the sample containing zone does not cause attenuation of radiation energy emitting to the front side of the samples, i.e. transmits at least approximately 95% of the radiation energy directed thereat.

The front side of the sample holding zone can be, for example, Vycor® glass (Corning Glass Works), or quartz.

The rear side of the sample containing zone is preferably of a material of construction which is porous to the extent of permitting passage of nitric oxide gas but not to the extent of permitting passage of protein, e.g., 40 micron pores, so as to separate liberated nitric oxide gas from protein so liberated nitric oxide gas cannot recombine with protein. The rear side of the sample containing zone is preferably of Vycor® glass.

The solvent containing zone except adjacent the rear side gas passage permitting portion of the sample holding zone, is constructed of an inert material, e.g. polytetrafluoroethylene and is preferably painted black except adjacent where nitric oxide gas is passing from the sample container (as explained later).

The solvent in the solvent containing zone is one that has a higher solubility for nitric oxide gas than the sample and is preferably methanol.

The electrochemical detection is with nitric oxide selective electrode which is an ion selective electrode that generates a small voltage (e.g., in the picovolt range) which is quantitatively proportional to this concentration of nitric oxide dissolved in solvent when immersed in the solvent with nitric oxide dissolved therein.

We turn now to calibration of the response provided by the electrode with amount of nitric oxide gas released and dissolved in the solvent. Nitrosoglutathione can be used to calibrate for photolysis of amount of nitric oxide from nitrosothiols and sodium nitroprusside can be used to calibrate for photolysis of amount of nitric oxide from iron nitrosyls and both cover the range of amounts of nitric oxide from the combined nitric oxide. Nitric oxide selective electrodes are commercially available.

In a preferred method of the second embodiment, the blood sample is loaded into the sample containing zone with and/or without nitrosothiol degrading agent therein, e.g. by pricking a finger with a lancet or other sharp and loading the sample into the sample containing zone, for example, by capillary action, solvent is introduced into a solvent containing zone, the rear side of the sample containing zone is positioned adjacent the solvent containing zone, followed by positioning a low power electromagnetic radiation emitter (low power laser or low power light-emitting diode) up to 12 inches away from the sample containing zone and irradiating sample in the sample containing zone with the electromagnetic radiation emitter emitting a beam of cross-sectional area corresponding to the cross-sectional area of the sample. The electrode is lowered into the solvent containing zone and detects a generated voltage corresponding to the amount of nitric oxide in the solvent containing zone. Electromagnetic radiation beam is directed at the sample for as long as nitric oxide gas increase is detected, whereupon the electromagnetic radiation source is turned off and the electrode is raised out of contact with the solvent whereupon apparatus providing the sample containing zone may be discarded.

The generated voltage detected by the electrode is in the picovolt range and is amplified using a DC amplifier for measurement, e.g., using a voltmeter. A signal integrator can be present in the system to quantify the area under any peak. Signal from the amplifier and/or signal integrator may feed into an analog to digital converter which passes a signal to a computer or volt meter or other digital interface to provide digital or graphical readout indicating amount of combined nitric oxide, that is total nitric oxide present as nitrosothiols and iron nitrosyls (no nitrosothiol destroying agent used), or amount of nitric oxide present as iron nitrosyls (nitrosothiol destroying agent used).

The electromagnetic radiation can be 300-400 nm wavelength ultraviolet radiation provided by an ultraviolet laser or ultraviolet light-emitting diode as described in conjunction with the first embodiment or a 210-220 nm wavelength ultraviolet radiation provided by an appropriate ultraviolet light emitting diode as described in conjunction with the first embodiment or visible light (500 to 600 nm wavelength) radiation provided by a light-emitting diode as described in conjunction with the first embodiment or near infrared radiation provided by a mean infrared light-emitting diode as described in conjunction with the first embodiment, and the front side of the sample containing zone is transparent to whichever electromagnetic radiation is emitted in the direction of the sample containing zone to allow passing of the electromagnetic radiation into the sample containing zone and cause liberation of nitric oxide from the sample.

We turn now to the third embodiment herein.

A preferred system for carrying out the method of the third embodiment is depicted in FIGS. 1-5.

With reference to FIG. 1, there is schematically depicted a disposable phlebotomy cassette 10 which contains blood sample containing chambers 12 and 14 which both constitute sample containing zones. A front wall 16 of cassette 10 is of Vycor® glass or other electromagnetic radiation transparent material (i.e. to whichever kind of electromagnetic radiation is used) and a rear wall 18 of the cassette is constituted, for example, of Vycor® glass (40 micron pores) and reliance is placed on the rear wall's property of being porous to nitric oxide gas but preventing passage therethrough of protein. The blood sample containing chamber 12 is impregnated with mercury (II) chloride or other nitrosothiols destroying agent so as not to interfere with absorption of electromagnetic radiation by blood sample. Blood sample containing chambers 12 and 14 are, for example, 4 mm diameter and 5 mm transverse dimension. The chamber 12 contains nitrosothiols destroying agent, e.g. mercury (II) chloride, in large excess, compared to nitrosothiols that are present; the chamber 14 does not contain nitrosothiols destroying agent.

Communicating with chamber 12 is a capillary blood sample containing chamber/zone inlet 20. Communicating with chamber 14 is a capillary blood sample containing chamber/zone inlet 22.

Figure 2:
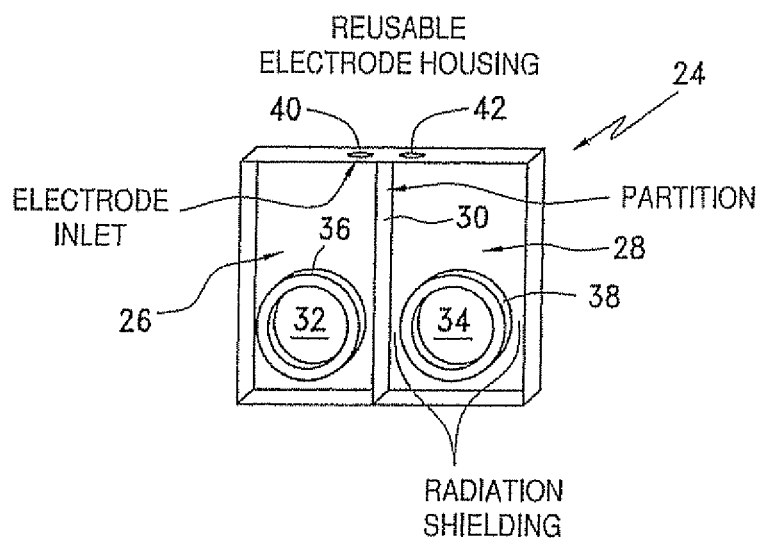
FIG. 2 depicts a reusable housing for holding solvent and for insertion of electrode, for use in association with the cassette of FIG. 1.

With reference to FIG. 2, there is schematically depicted a reusable solvent reservoir/electrode introduction compartment or housing 24 which provides a solvent containing zone and which is constructed of inert material (i.e., inert to solvent and nitric oxide gas), e.g. polytetrafluoroethylene. The element 24 contains two solvent reservoir compartments 26 and 28 separated by a partition 30. The element 24 contains a solid back wall and a front wall with circular openings 32 and 34, respectively, into each of the compartments 26 and 28. The opening 32 is bounded by a ring shaped upstanding protruding wall 36, and the opening 34 is bounded by ring shaped upstanding protruding wall 38. An upper wall of element 24 is provided with an opening 40 for introduction of an electrode into compartment 26 and an opening 42 for introduction of electrode into compartment 28. Each of the upstanding walls 36 and 38 is colored black or otherwise provided with electromagnetic radiation shielding to minimize and guard against electromagnetic radiation scattering to inserted electrode (described later) since electromagnetic radiation affects the voltage detected by an electrode.

The disposable cassette 10 and solvent reservoir/electrode introduction compartment 24 are assembled, for example, by clamping cassette 10 to solvent reservoir/electrode introduction compartment 24 so the rear side of cassette 10 adjacent chambers 12 and 14 is contiguous with openings 32 and 34 (FIG. 2). Alternatively, cassette 10 can be attached to element 24 by providing retaining brackets on the front side of element 24 or by providing structure on the front of element 24 providing an insertion slot for assembling cassette 10 and element 24. The assembly provided is schematically depicted in FIG. 3 which is denoted 58.

Figure 3:
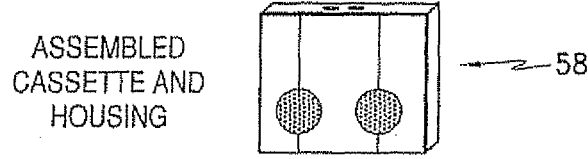
FIG. 3 depicts an assembly of the cassette of FIG. 1 and the housing of FIG. 2.
Figure 4:
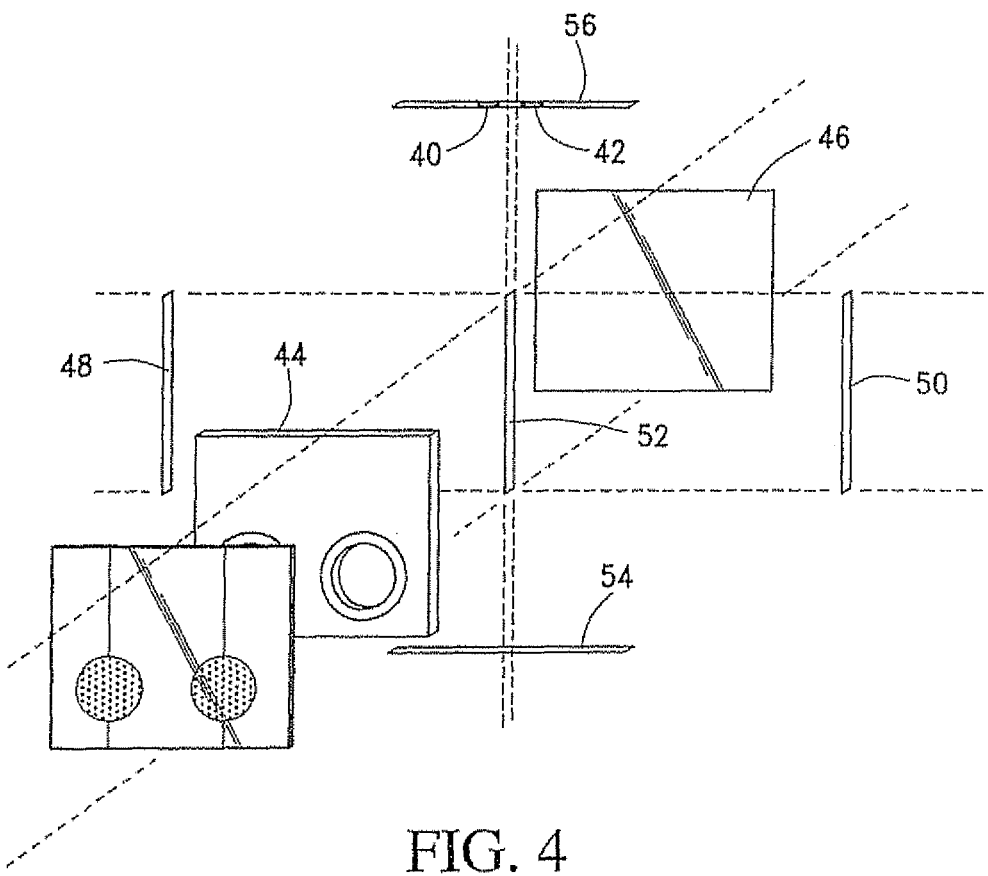
FIG. 4 is an exploded view of the assembly of FIG. 3 showing some interior details.

FIG. 4 depicts an exploded view of the assembly of FIG. 3, and indicates the cassette 10 positioned in front of a front wall 44 of element 24. The front wall 44 is forward of rear wall 46 of element 24. Element 44 contains a left side wall 48, a right side wall 50, an interior vertical wall 52 dividing element 24 into compartments 26 and 28 (depicted in FIG. 2), a bottom wall 54 and a top wall 56 containing electrode insertion openings 40 and 42 (also depicted in FIG. 2).

Figure 5:
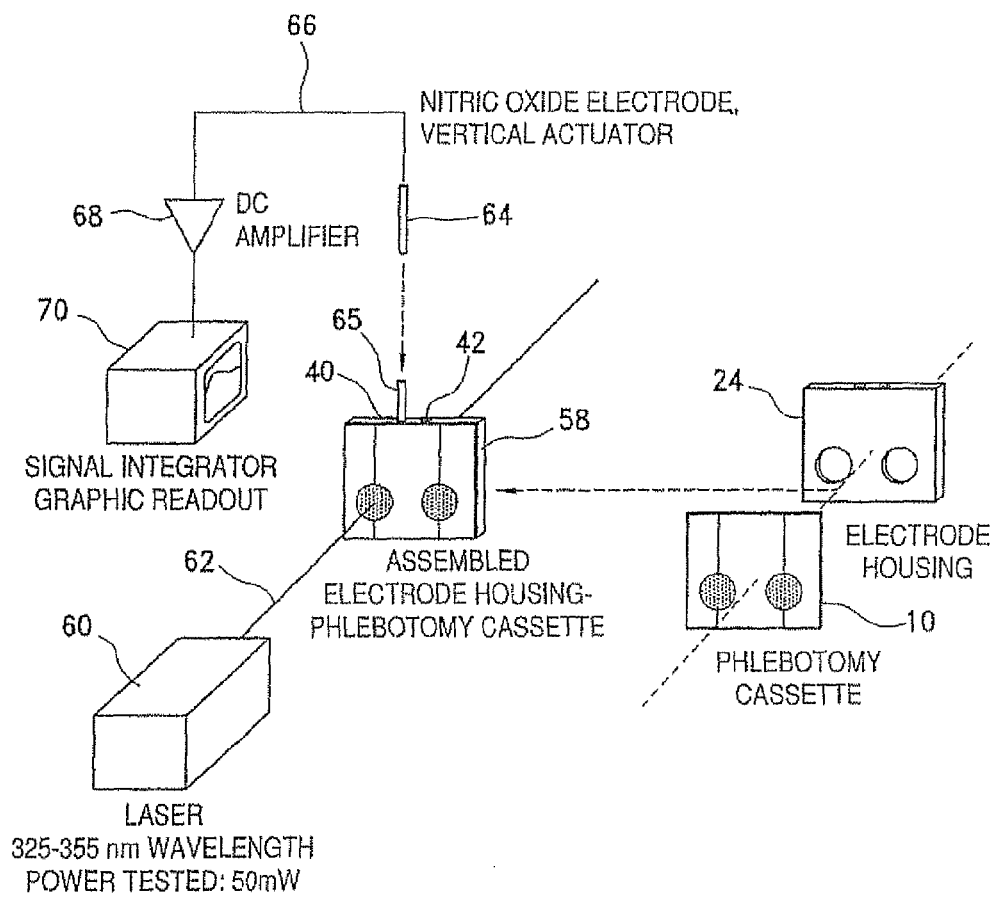
FIG. 5 is a schematic of apparatus for a method of the third embodiment.

FIG. 5 depicts phlebotomy cassette 10 (see also FIG. 1), solvent reservoir/electrode introduction compartment 24 (see also FIG. 2), assembly 58 (see also FIG. 3) as well as an electromagnetic radiation source depicted as a laser source 60 which directs a laser beam 62 of 325-355 nm frequency and 50 milliwatts power, e.g. a $Nd:Y_3A_{15}O_{12}$ laser, at one of the sample containing compartments 12 and 14, from a distance, for example, of 6 to 10 inches, providing a laser beam of cross-sectional area at assembly 58 coextensive with the inlet opening of a sample containing compartment (12 or 14) to which it is directed.

Also depicted in FIG. 5 is a nitric oxide selective electrode 64 provided with a vertical actuator (not shown) which can be operated by a computer to raise or lower the electrode 64 into the appropriate electrode insertion opening (40 or 42). The electrode 64 is shown inserted into compartment 26 (FIG. 2) at 65 (FIG. 5).

The electrode 64 is a nitric oxide selective electrode detecting voltage generated by presence of nitric oxide gas in solvent in 24 and providing a signal 66 in picovolts to a DC amplifier 68 which in turn provides an amplified signal 70 to a signal integrator, and to a graphic readout device 70 which provides readout of amount of nitric oxide dissolved in solvent corresponding to amount of nitric oxide present as combined nitric oxide.

In use, finger of patient for whom blood nitric oxide data is desired, is pricked with a lancet, e.g. at bedside, to provide blood flow by capillary action through channels 20 and 22 respectively into chambers 12 and 14 (FIG. 1). Then element 24 (FIG. 2) laid flat with rings 36 and 38 facing up, is filled through openings 32 and 34 with solvent that is of higher solubility for nitric oxide gas than the blood sample, preferably methanol. The cassette 10 is then assembled with element 24 so compartments 12 and 14 are opposite openings 32 and 34 respectively, e.g. by clamping cassette 10 to element 24 so that windows for compartments 12 and 14 are in front of the cassette 10. Then laser 60 (FIG. 5) is turned on to provide beam of ultraviolet laser irradiation of 325-355 nm of intensity high enough to maximize nitric oxide that is liberated (i.e. is the intensity sufficient to break bonds to nitric oxide) but not so large as to break down or otherwise interfere with providing liberated nitric oxide) into compartment 12 or compartment 14, e.g. 50 milliwatts power. Electrode 64 (FIG. 5) is lowered into solvent reservoir 26 after the laser beam of laser 60 is directed at sample compartment 12 and raised from compartment 12 after electrochemical detection of released nitric oxide, and lowered into solvent reservoir 28 after the laser beam of laser 60 is directed at sample compartment 14 and raised from compartment 14 after electrochemical detection of released nitric oxide. The raising and lowering of electrode 64 into compartments 26 and 28 is preferably by computer activation of driving motor (not shown). Separate measurements are obtained in succession in either order.

The nitrosothiol destroying agent in compartment 12 degrades (selectively cleaves) the nitrosothiols therein to nitrous acid from which nitric oxide is not liberated by electromagnetic radiation.

When the laser beam 62 is aimed at compartment 12, electrode 64 is lowered through opening 40 into solvent compartment 26. The laser treatment liberates gaseous nitric oxide from iron nitrosyls in the sample in compartment 12 which passes from compartment 12 to diffuse through the porous back wall of cassette 10 into compartment 26 where the liberated nitric oxide is dissolved in the solvent in chamber 26. Laser irradiation is continued for as long as reading on readout at 70 increases. The readout indicates the amount of nitric oxide present as iron nitrosyls in the sample.

When the laser beam 62 is aimed at compartment 14, electrode 64 is lowered through opening 42 into solvent compartment 28. The laser treatment liberates nitric oxide from iron nitrosyls and also from nitrosothiols. The liberated nitric oxide passes through the porous back wall of cassette 10 into solvent reservoir 28 whereby amount of dissolved nitric oxide is detected to provide readout at 70 of total nitric oxide present as combined nitric oxide.

The porous back wall of cassette 10 allows passage of nitric oxide gas into solvent containing zones but no protein so irradiation causes continuous release of nitric oxide without any rebinding to protein.

The determination of total nitric oxide present as combined nitric oxide and of nitric oxide present as iron nitrosyls allows computation of ratio of nitric oxide present as iron nitrosyls to total nitric oxide, i.e. present as combined nitric oxide, and by difference determination of amount of nitrosothiols in a sample thereby providing data allowing diagnosis and/or confirmation of diagnosis.

For the third embodiment, the laser 60 can be replaced by a light-emitting diode that emits 210-220 nm wavelength ultraviolet radiation or 300-400 nm wavelength ultraviolet radiation or 500-600 nm wavelength visible radiation or 700-1400 nm wavelength near-infrared radiation with excellently comparable results.

Variations

The foregoing description of the invention has been presented describing certain operable and preferred embodiments. It is not intended that the invention should be so limited since variations and modifications thereof will be obvious to the skilled in the art, all of which are within the spirit and scope of the invention.

What is claimed is:

1. A method for liberating nitric oxide gas from nitrosothiols and iron nitrosyls in a blood sample, comprising the steps of:
   (a) introducing the blood sample into a sample containing zone having a front side which is electromagnetic radiation transparent and a rear side which is porous to the extent of permitting nitric oxide gas to pass therethrough while preventing protein from passing therethrough; and
   (b) directing electromagnetic radiation of less than 100 milliwatts at said front side to cause liberation of nitric oxide gas from the nitrosothiols and iron nitrosyls and passage of the liberated nitric oxide gas from said rear side.

2. The method of claim 1 where the electromagnetic radiation is ultraviolet radiation.

3. The method of claim 2 where the ultraviolet radiation has a wavelength ranging from 300 to 400 nm.

4. The method of claim 3 where the ultraviolet radiation has a wavelength ranging from 325 to 355 nm.

5. The method of claim 2 where the ultraviolet radiation has a wavelength ranging from 210 to 220 nm.

6. The method of claim 1 where the electromagnetic radiation is visible electromagnetic radiation having a wavelength ranging from 500 to 600 nm.

7. The method of claim 1 where the electromagnetic radiation is near-infrared radiation.

8. The method of claim 1 where the electromagnetic radiation is from a laser.

9. The method of claim 1 where the electromagnetic radiation is from a light-emitting diode.

10. The method of claim 1 wherein the method further comprises the following steps:
    (c) providing a solvent containing zone to dissolve the liberated nitric oxide gas that has passed through said rear side where the solvent is one that dissolves nitric oxide gas;
    (d) electrochemically detecting the amount of dissolved nitric oxide gas in the solvent which corresponds to the total amount of nitric oxide present as nitrosothiols and iron nitrosyls in the sample.

11. The method of claim 1, where the electromagnetic radiation is in the range of from 30 to 60 milliwatts.

12. The method of claim 11, where the electromagnetic radiation is 50 milliwatts.

* * * * *